United States Patent [19]

Graham

[11] Patent Number: 4,584,188

[45] Date of Patent: Apr. 22, 1986

[54] HYDROGELS

[75] Inventor: Neil B. Graham, Bearsden, Scotland

[73] Assignee: Nationale Research Development Corporation, London, England

[21] Appl. No.: 677,473

[22] Filed: Dec. 3, 1984

[30] Foreign Application Priority Data

Jun. 12, 1981 [GB] United Kingdom ............... 8118088
Jun. 12, 1981 [GB] United Kingdom ............... 8118089
Jun. 12, 1981 [GB] United Kingdom ............... 8118090

Related U.S. Application Data

[62] Division of Ser. No. 569,263, Jan. 9, 1984, which is a division of Ser. No. 387,817, Jan. 14, 1982, Pat. No. 4,438,258.

[51] Int. Cl.$^4$ .................... A01N 25/26; A61J 3/00
[52] U.S. Cl. .................... 424/19; 523/105; 523/111; 523/113; 523/115; 523/122; 524/593; 525/50; 525/529; 528/271; 528/361; 528/392
[58] Field of Search ................ 424/19; 523/122

[56] References Cited

U.S. PATENT DOCUMENTS

| | | | |
|---|---|---|---|
| 3,322,740 | 5/1967 | Kiff et al. ............ | 528/392 |
| 3,812,071 | 5/1974 | Stoy ............ | 524/796 |
| 3,927,206 | 12/1975 | Blank et al. ............ | 424/81 |
| 3,975,350 | 8/1976 | Hudgin et al. ............ | 424/78 |
| 4,056,502 | 11/1977 | Gross ............ | 524/833 |
| 4,150,108 | 4/1979 | Graham ............ | 424/22 |
| 4,177,056 | 12/1979 | Mueller et al. ............ | 424/78 |
| 4,192,827 | 3/1980 | Mueller et al. ............ | 525/123 |
| 4,202,880 | 5/1980 | Fildes et al. ............ | 424/78 |
| 4,221,779 | 9/1980 | Graham ............ | 524/78 |
| 4,226,848 | 10/1980 | Nagai et al. ............ | 424/19 |
| 4,267,295 | 5/1981 | Gallop et al. ............ | 526/264 |

FOREIGN PATENT DOCUMENTS

| | | |
|---|---|---|
| 0000291 | 10/1979 | European Pat. Off. . |
| 1022438 | 3/1966 | United Kingdom . |
| 1035877 | 7/1966 | United Kingdom . |
| 1439069 | 6/1976 | United Kingdom . |
| 1445137 | 8/1976 | United Kingdom . |
| 1458584 | 12/1976 | United Kingdom . |
| 1489965 | 10/1977 | United Kingdom . |
| 1556584 | 11/1979 | United Kingdom . |
| 2047093 | 11/1980 | United Kingdom . |

*Primary Examiner*—John Kight
*Assistant Examiner*—M. L. Moore
*Attorney, Agent, or Firm*—Oblon, Fisher, Spivak, McClelland & Maier

[57] ABSTRACT

A hydrogel which comprises polymerized moieties derivable from (i) at least one polymerizable cyclic (thio)ether and (ii) at least one hydrophilic homo- or copolymer.

12 Claims, 9 Drawing Figures

HYDROGELS

This is a division of application Ser. No. 569,263, filed Jan. 9, 1984.

BACKGROUND OF THE INVENTION

1. Field of the Invention

This invention relates to hydrogels; more particularly, but not exclusively, this invention relates to hydrogels which may be used as interfaces between damaged outer human and animal tissue, such as epidermal or epithelial tissue (hereinafter termed a wound) and its external environment.

This invention also relates to controlled release compositions comprising the hydrogels and an active substance, for example a medication system; to processes for preparing the controlled release compositions; and to methods of utilising the medications thereof, especially in vivo.

2. Description of the Prior Art

In the treatment of burns or other (post-operative, accidental or dermatological) tissue damage it is highly desirable to provide such an interface as aforesaid. Ideally, the interface should protect the wound from physical trauma; from agents of infection, such as airborne fungi, bacteria and viruses, gaining access to the wound; should prevent maceration of the scab and healing tissue by controlling the moisture of the wound. In addition, if desired, the medication should also maintain medication in contact with the wound.

Present gauze dressings such as leno weave dressings, are opaque after application and need frequent change to observe the healing process and to apply medication. This causes patient discomfort, particularly where wound exudate has dried and consolidated the dressing and the wound. Moreover, they do not exclude agents of infection, nor do they control the moisture of the wound: it is simply absorbed.

Hydrogels have already been indicated for use as a wound dressing but these have generally been natural and semi-synthetic products such as collagen, gelatin and starch products. These materials are not normally transparent; moreover, proteinaceous hydrogels can be allergenic; furthermore, they do not control the agents of infection, indeed, they may provide a nutrient source.

SUMMARY OF THE INVENTION

The present invention provides a hydrogel which comprises polymerised moieties derivable from (i) at least one polymerisable cyclic (thio)ether and from (ii) at least one hydrophilic homo- or copolymer.

DESCRIPTION OF THE INVENTION

In accordance with one aspect of this invention, the present hydrogel is hydrolysable in aqueous media. The or each hydrolysable function may be contained in (i) or (ii) or in both (i) and (ii). Suitably, the hydrogel comprises a hydrolysable carboxylic ester, carbonate ester, amide, urethane or glycoside function.

Desirably, the polymerisable cyclic (thio)ether (i) may comprise a compound of the formula:

in which:

$R_1$, $R_2$ and $R_4$, which may be the same or different, each represent a hydrogen atom or a substituted or unsubstituted hydrocarbyl or hydrocarbyloxy group;

$R_3$ represents a substituted or unsubstituted methylene, ethylene or 1,3-propylene group;

$R_5$ represents a monovalent polymerisable group;

Q represents an oxygen or a sulphur atom; and

X represents:

in which:

Y represents an oxygen atom or an $—NR_6—$ group wherein $R_6$ represents any of the values which $R_1$ may assume;

a is 0 or 1;
b is 0 or 1;
c is 1 or 2;
d is 0 or 1;

with the proviso that at least one of b or d is 1.

Particularly preferred polymerisable cyclic ethers have the formula:

$R_5$ may suitably represent any monomeric, oligomeric or polymeric group provided that it comprises a polymerisable group; that is a group which can participate in the cationic polymerisation to form the hydrogel, either to react with the polymerisable cyclic (thi-o)ether or the hydrophilic homo- or copolymer or, indeed, both. Preferred examples, which react with both moieties, are vinyl (thio)ether and epoxy groups.

It is particularly preferred that $R_5$ represents a cyclic vinyl (thio)ether, especially of the formula:

in which:

$R_1'$, $R_2'$, $R_3'$ and $R_4'$, which may be the same or different, represent any of the values which $R_1$, $R_2$, $R_3$ and $R_4$ may assume;

M represents the group $—ZX'—$;

Q' represents any oxygen or sulphur atom;

X' represents any of the values which X may assume; and

Z represents a single bond or a carbon-linked mono-, oligo-, or homo- or co-poly (substituted or unsubstituted alkylene or alkylene oxide) group.

Especially preferred polymerisable cyclic ethers are the reaction products formed by subjecting one or a mixture of dihydropyran aldehydes to disproportionation by the Tischenko reaction; they have the formula:

in which: $R_1'$, $R_2'$, and $R_4'$, which may be the same or different, represent any of the values which $R_1$, $R_2$, and $R_4$ respectively may assume. A preferred such compound is the acrolein tetramer in which $R_i$ all represent hydrogen atoms.

Polymerisable cyclic ethers wherein X comprises a —COO— or —CH$_2$OCO— group may conveniently be prepared from the tetramer of the corresponding unsaturated aldehyde produced by the Tischenko reaction. Namely:

Cyclic ethers wherein X comprises a —COO— group may be prepared by reacting the tetramer with an alcohol R$_5$OH using a transesterification catalyst and reaction conditions:

Cyclic ethers wherein X comprises a —CH$_2$OCO— group may be prepared by reaction of the tetramer with a lower alkyl carboxylic acid ester R$_5$COOR$_9$ wherein R$_9$ represents a lower alkyl group using a transesterification catalyst and reaction conditions:

The respective by-products may also be esterified with R$_5$COOH$_9$ or R$_5$OH to give, correspondingly:

The corresponding amides may be prepared analogously.

Cyclic ethers where X comprises a —COO— group may also be obtained by mild oxidation of the dimer of the corresponding unsaturated aldehyde, followed by esterification of the salt for example the silver salt.

Meta-carbonates and oxalates may be obtained, respectively, by esterification:

It is, however, to be stressed that the acrolein tetramer is readily prepared from acrolein which is a commercially available material, can readily be purified and has been found to be satisfactory in the practice of this invention.

The polymerisable cyclic (thio)ether (i) may also comprise a compound of the formula:

in which: $R_1$, $R_2$, $R_3$, $R_4$, $R_5$, and Q are as hereinabove defined; and X represents:

in which:
Y represents an oxygen atom or an —NR$_6$— group wherein
R$_6$ represents any of the values which R$_1$ may assume;
a is 0 or 1;
b is 0 or 1;
c is 0 or 1;
with the proviso that b+c is 1.

The polymerisable cyclic (thio)ether (i) may also comprise the aldol condensation product of at least one dimer of the corresponding unsaturated aldehyde:

namely:

The polymerisable cyclic (thio)ether (i) may further comprise the Diels-Alder product obtained by reacting at least one unsaturated aldehyde with a polyvinyl ether of a polyhydroxy compound:

wherein: $R_7$ represents an n-valent hydrocarbon or poly(oxyhydrocarbon) residue of an n-hydroxy compound.

The polymerisable cyclic (thio)ether (i) may further comprise wherein: $R_8$ represents an n-valent non-hydrolysable bridging residue.

These last four depicted compounds give rise to hydrogels which are less readily hydrolysed. Their use gives a first method for providing a hydrogel according to the invention with a desired rate of hydrolysis.

The degree of hydrolytic stability provided can also be accurately tailored by a number of other different mechanisms. Thus, homologues of the acrolein tetramer, for example methacrolein tetramer or the mixed acrolein/methacrolein tetramer, exert steric hindrance, which increases as the size of $R_4$ increases, to the hydrolysable ester or amide function X and thereby increases the stability of the derivative. Mono-, di and poly-carboxy and phenolic hydroxy substituted hydrocarbons form derivatives which are prone to hydrolysis and which yield catalytic acidic species thereon; derivatives wherein X and X', which may be the same or different, each represent a —COO— or —CH₂OCO— group and Z represents a substituted or unsubstituted hydrocarbylene group also facilitate hydrolysis. Furthermore, derivatives which retain one or more carboxy or hydroxy groups comprise a relatively high level of water which itself facilitates hydrolysis.

The groups $R_1$, $R_2$ and $R_4$ may each represent a substituted or unsubstituted hydrocarbyl or hydrocarbyloxy group. Examples include unsubstituted or halo-substituted $C_1$ to $C_4$ alkyl, such as methyl or ethyl; unsubstituted $C_6$ to $C_{10}$ aryl or aralkyl such as phenyl or benzyl; and oxy analogues. In the case of $R_4$, increase in the size of the group increases the steric hindrance to any hydrolysable ester or amide function and thereby increases the stability of the hydrogel. It is preferred, however, from the standpoint of ease of preparation and availability, that at least one, and preferably all, of $R_1$, $R_2$ and $R_4$ represents a hydrogen atom. The group $R_3$ may represent a mono- or poly-substituted ethylene group, preferably an unsubstituted ethylene group; that is, a dihydro(thia)pyran derivative.

Preferred such compounds (i) are ethers; that is, those compounds of the above formula wherein Q represents an oxygen atom, especially dihydropyrans.

Suitable hydrophilic homo- or copolymers (ii) comprise residues derivable from at least one of the following monomer classes:

(a) meth)acrylic acid, (meth)acrylamide, an unsubstituted or hydroxy-substituted ethyl or propyl (meth)acrylate, or a poly(oxyethylene)ester of (meth)acrylic acid;

(b) a substituted or unsubstituted cyclic mono or poly ether having from 3 to 6 rings atoms or a cyclic imine having 3 rings atoms; or (c) a substituted or unsubstituted vinyl alcohol, aldehyde, ether, acetal, ketone, ester, or substituted or unsubstituted N-vinyl heterocyclic compound.

By "(meth)acryl" we mean herein: "methacryl" or "acryl" or both.

The monomers in class (b) include epoxides such as ethylene oxide, propylene oxide, 1,2-epoxybutane, 2,3-epoxybutane glycidyl ethers, N-(epoxy substituted) heterocyclic compounds such as N-(2,3-epoxypropyl)-pyrrolidone. Epihalohydrins, while not themselves cyclic ethers, do give homo- and copolymers derivable therefrom. Examples of these include epifluorohydrin, epichlorohydrin and epibromohydrin. Other cyclic mono- or poly ethers include oxetane, tetrahydrofuran, dihydrofuran, dihydropyran, dioxolane and trioxane. Homo- and copolymers derivable therefrom include partially $C_1$ to $C_4$ alkyl etherified celluloses and starches, homo- and copoly(alkylene oxides) which may be cross-linked through urethane or unsaturated cyclic ether groups such as polyoxymethylene, polyethylene glycols and polypropylene glycols, and polyesters thereof with dicarboxylic acids such as maleic acid.

The monomers in class (c) include methyl and ethyl vinyl ether, methyl vinyl ketone, methallyl alcohol, N-vinyl pyrrolidone, N-vinyl carbazole, N-vinyl pyridine, N-vinyl oxazole, N-vinyl methyloxazolidone, vinyl formal, vinyl butyral, vinyl methoxyacetal. Homo- and copolymers derivable therefrom include polyvinyl acetate and polyvinyl alcohol.

A group of preferred hydrophilic homo- or copolymers are derivable from class (b) monomers and desirably comprise polymerised alkylene oxide, especially ethylene oxide, residues. Preferably, the hydrophilic homo- or copolymer is a homo- or copoly(alkylene oxide), (especially a homo- or copoly(ethylene oxide).

Particularly preferred are homo- or "blocky" copoly(alkylene oxide)s which comprise polyethylene oxide residues having a ratio of number average molecular weight to functionality (hereinafter termed "equivalent weight") greater than 750, preferably greater than 1,000. Although equivalent weights as low as 500 to 250 or even less may be used, such polymers tend to be less swellable.

For use as wound dressings, it is preferred that the homo- or copoly(alkylene oxide)s comprise polyethylene oxide residues having an equivalent weight from 1,200 to 1,800, preferably about 1,400 to 1,600, are used. For use in controlled release compositions, it is preferred that the homo- or copoly(alkylene oxide)s comprise polyethylene oxide residues having an equivalent weight from 1,200 to 4,000 or higher, preferably about 1,500 to 3,000 such as 2,000 or more are used.

Especially preferred hydrophilic polymers (ii) are poly(ethylene oxide)s having an equivalent weight as aforesaid.

Hydrogels prepared therefrom are found to be crystalline in the dry form and to exhibit syneresis in the wet from, both of which properties are utilised to advantage in this invention, as will subsequently be explained.

Hydrophilic homo- or copolymers comprising polymerised alkylene oxide residues are conveniently prepared by the addition polymerisation of an alkylene oxide (a), such as ethylene oxide, with a compound (b) containing a reactive hydrogen atom, for example an aliphatic or aromatic hydroxyl, carboxyl, amino or mercapto compound. This compound may itself by a polymer or an oligomer, which will lead to blockiness in the resulting hydrophilic copolymer. This compound may also be a monomer, which will lead to a homopolymer (where only one alkylene oxide is polymerised) or a random copolymer (where a mixture of alkylene oxides is polymerised). In the former case the reactant polymer or oligomer may itself be a homo- or copoly(alkylene oxide).

Compounds (b) include those di-, tri-, tetra- or even higher substituted with reactive hydrogen containing functions; these may be monomeric, oligomeric or polymeric. More than one type of active hydrogen containing function may be present in compound (b) with hydroxyl and carboxyl, especially hydroxyl, groups being preferred. Aliphatic such compounds are particularly preferred. Mixtures of compounds (b) may be used.

Examples of di-carboxy or hydroxy compounds (b) include dicarboxylic acids, dihydric phenols, hydroxyacids and glycols, desirably those with less than 18, preferably less than 10, carbon atoms; for example oxalic, malonic, succinic, glutaric and adipic acids, 1,2-cyclohexanedicarboxylic, 1,3-cyclohexanedicarboxylic and 1,4-cyclohexanedicarboxylic acids, phthalic, isophthalic and terephthalic acids, 4,4'-dihydroxyphenyl-2,2-propane, resorcinol, quinol and orsinol, lactic, 2-hydroxyisobutyric, 10-hydroxydecanoic, 12-hydroxyoctadecenoic, 12-hydroxy-cis-9-octadecenoic, 2-hydroxycyclohexane carboxylic, 2-hydroxy-2-phenyl (D) propionic, diphenylhydroxyacetic, 2-hydroxybenzoic, 3-hydroxybenzoic and 4-hydroxybenzoic acids, glycol, propanediols and butanediols. Glycols are most suitable, especially the $C_2$ to $C_6$, preferably $C_2$ to $C_4$ glycols.

Mixtures of dicarboxylic acids, dihydric phenols, hydroxy acids and glycols may be used. Preferably the dicarboxylic acids, dihydric phenols, hydroxy acids and glycols are linear.

Examples of compounds (b) substituted by more than two carboxy or hydroxy groups include polycarboxylic acids, polyhydric phenols, hydroxy acids and polyhydric alcohols, desirably those with less than 18, preferably less than 10, carbon atoms; for example aliphatic polyols such as glycerol, erythritol, pentaerythritol, sorbitol, dulcitol, inositol, 2-ethyl-2-hydroxy-methyl-propane-1,3-diol and 1,2,6-hexanetriol; aromatic polyols such as 1,2,3-trihydroxybenzene, 1,2,4-trihydroxybenzene, 1,3,5-trihydroxybenzene; araliphatic polyols; hydroxy aliphatic, alicyclic and aromatic carboxylic acids, including Krebs cycle acids, such as citric acid, malic acid, tartaric acid, 2-hydroxy-3-methyl (D) succinic acid, ascorbic acid, 2,3-dihydroxybenzoic acid, 2,4-dihydroxybenzoic acid, 2,5-dihydroxybenzoic acid, 2,6-dihydroxybenzoic acid, 2,3,4-trihydroxybenzoic acid, 2,4,5-trihydroxybenzoic acid, 2,4,6-trihydroxybenzoic acid and 3,4,5-trihydroxybenzoic acid.

Mixtures of polycarboxylic acids, polyhydric phenols, hydroxy acids and polyhydric alcohols may be used. Preferably the polycarboxylic acids, polyhydric phenols, hydroxy acids and polyhydric alcohols are linear.

Further examples, some of which may be oligomeric or polymeric, include materials which are well known to those skilled in the art of rigid and flexible foam manufacture and comprise oxypropylated triols, tetrols and sugars, as well as polyesters. In general, however, low molecular weight compounds (b) are preferred since those of higher molecular weight can give compatibility problems which make the preparation of the hydrogel more difficult.

Where the hydrophilic polymers (ii) are copolymers comprising polymerised alkylene oxide residues, typically prepared as aforesaid, it is desirable that they comprise a minor amount only of component(s) additional to ethylene oxide, for example a higher alkylene oxide such as propylene oxide or butylene oxide. Typically, this minor amount will be small, suitably no more than 20%, preferably no more than 10% by weight or even less of the copolymer. Such copolymers are, however, of less interest since poly(ethylene oxide) possesses unique properties among the poly(alkylene oxides) arising from its hydrophilic character which renders it of particular value in the present invention. Accordingly, in accordance with a preferred feature of this invention, the hydrophilic polymer is a poly(ethylene oxide) which is the reaction product of:

(a) ethylene oxide with
(b) an aliphatic or aromatic hydroxyl, carboxyl, amino or mercapto compound.

One or more of components (i) may be polymerised with one or more of components (ii).

The polymerisable cyclic (thio)ether (i) and hydrophilic homo- or copolymer (ii) are polymerised to form a hydrogel. Usually, but not necessarily, (i) and (ii) are chemically cross-linked to form the hydrogel. They may instead either be polymerised to form a linear high molecular weight material which is then dispersed in a further polymerisable system which is thereafter polymerised to trap the said polymerised high molecular weight material in a entanglement network; alternatively, they may be polymerised to form a copolymer with hydrophobic blocks to give an amphipathic material. It is preferred, however, that chemical cross-linking occurs.

Chemical cross-linking may be effected by incorporating into the hydrogel a compound which contains at least three groups which can participate in the cationic polymerisation. Preferably the chemical cross-linking is effected by incorporating into the hydrogel a compound with more than two active hydrogen atoms. Such compounds include tri-, tetra- or even higher substituted aliphatic or aromatic hydroxyl, carboxyl, amido, or mercapto compounds. These include any of the above-mentioned compounds (b) which have more than two active hydrogen atoms. Indeed, it is possible to utilise the corss-linking compound as compound (b) to form the homo or co(polyalkylene oxide). The cross-linking compound may instead be incorporated as such into the polymerisation mixture.

The chemical cross-linking may also be effected by incorporating into the hydrogel a compound comprising more than two polymerisable cyclic (thio)ether groups. Examples of such compounds include the reaction products of stoichiometric amounts of a substituted or unsubstituted acrolein tetramer with tri-, tetra- or even higher substituted aliphatic or aromatic hydroxyl, carboxyl, amino or mercapto compounds; for example, the product obtained by transesterifying acrolein tetramer with a polyhydric alcohol such as glycerol.

The hydrogel may also be chemically cross-linked with a compound which contains one polymerisable cyclic (thio)ether group and two reactive hydrogen atoms or two polymerisable cyclic (thio)ether groups and one reactive hydrogen atom as in the case with the aldol condensation products mentioned earlier.

Incorporating a stoichiometric excess of (i) with the hydrogel also effects chemical cross-linking.

Mixtures of cross-linking agents may be used.

The hydrolysable hydrogel may be prepared by cationically polymerising at least one polymerisable cyclic (thio)ether (i) with at least one hydrophilic homo- or copolymer (ii) in the presence of at least one cross-linking agent, if required, and an acid catalyst.

Advantageously, the polymerisation is effected at an elevated temperature such as from 50° to 120° C., suitably from 60° to 100° C., especially from 70° to 90° C. Ambient or autogenous pressure may be used.

Suitable acid catalysts include both Bronsted and Lewis acids. The former include strong mineral acids which are not redox reagents under the polymerisation conditions, such as hydrochloric acid, sulphuric acid, tosylic acid, brosylic acid and the adduct of methanol and boron trifluoride. Suitable Lewis acids include boron trifluoride, boron trichloride, boron tribromide, aluminium trichloride, aluminium tribromide, gallium trichloride, germanium tetrachloride, tin tetrabromide, zinc chloride and ferric chloride, ferric chloride being preferred. From 0.01% to 2%, particularly from 0.04% to 1%, based on the total weight of the polymerisation mixture may suitably be used.

The molar proportion of components (i) : (ii) may vary between wide limits. However, it is a particularly preferred feature of this invention that the cyclic (thio)ether is in excess of the amount required by stoichiometry, typically an excess of 5 to 1000% by weight, preferably of 10 to 500% by weight, especially of 20 to 100% by weight. Surprisingly, it is found that when this is the case not only does the cyclic (thio)ether polymerise with itself but that also gross phase separation of the resulting polymer does not occur: rather, the system remains homogenous or domains of colloidal dimensions are formed which reinforce the hydrogel to give a controlled release composition of greatly enhanced physical strength.

This is of particular importance in the case of hydrogels in the form of films or more massive forms, for example as might be used in controlled release compositions: if it is attempted to make such materials from polymers comprising polyethylene oxide residues having an equivalent weight from 1200 to 1800 utilizing stoichiometric amounts of reactants, the resulting hydrogel will, in general, be weak both in the dry and in swollen states. This is an advantage in providing a comminuted product for a wound dressing agent. For other products it is highly desirable, to ensure that the product can withstand handling and swelling (for example, with active substance loading and release) to ensure an excess, preferably a substantial excess of component (i).

Such hydrogels have a very low order of toxicity; do not generate gas when formed in the presence of adventitious moisture, thin films and castings thus being readily prepared free from undesirable bubbles; and can tolerate substantial latitude in reactant proportions without changes in physical properties arising.

In addition, other compounds which can be cationically polymerised with (i) may also be incorporated into the polymerisation mixture, typically in an amount not greater than 30% by weight, preferably not greater than 20% by weight of the hydrogel. Examples include:

(a') linear mono- and poly- vinyl (thio)ethers, though these tent to impart a rapid rate of hydrolysis to the hydrogel;

(b') compounds comprising at least one 3 or 4-membered oxa or thia-substituted ring, such as mono- and polyepoxides;

(c') lactones with a 4-membered ring;

(d') cyclic aliphatic anhydrides including maleic anhydride;

(e') aliphatic aldehydes;

(f) furfural and furfural alcohol; and (g') mono- and poly-vinyl aromatic hydrocarbons, such as styrene, alkyl styrenes and divinyl benzene.

All of these compounds can provide a toughened composition by microscopic phase separation. Mixtures of such compounds may also be used.

In this specification the term hydrogel is used to denote a polymer which is swellable by aqueous media, the term being applicable to the polymer either in the unswollen or dry state or in the swollen or wet state.

Dry hydrogels can exhibit crystallinity and, as mentioned previously, this is the case where the hydrophilic polymer (ii) comprises poly(ethylene oxide) of equivalent weight greater than 1000 perferably greater than 2,000. The existence of crystallites in such hydrogels can make a further significant contribution, in addition to the above, to the strength of the dry, or swelling hydrogel.

The hydrogels of this invention desirably have a glass transition temperature from −120° C. to +15° C. and, when dry, a crystallite melting temperature from +10° C. to +60° C.

The hydrogels of this invention may be used as a supported or unsupported film. In the former case, the support may be contiguous, preferably transparent, backing member or a mesh, for example of nylon, about which the hydrogel has been polymerised. Particularly, in the case of hydrogels toughened by microscopic phase separation the film may be unsupported.

The hydrogels may also be spun as fibres and woven into a fabric.

Finally, and most preferred, the hydrogels may be used as a powder. The powder may be formed as such in the polymerisation, as disclosed in our Specification No. 8138713 or may be comminuted after formation as disclosed in our specification No. 8118087.

In accordance with a further aspect of this invention, there is provided a controlled release composition which comprises an active substance, particularly a biologically active substance, for example a medication system, and a carrier therefor comprising a hydrogel as herein described.

By "medication system" is meant any physiologically active substance or substances which it is desired, either by way of prophylaxis or therapy, to provide in vivo.

The present invention is of broad applicability in the formulation of active substances, particularly, but not exclusively, in the formulation of biologically active substances releasable at a controlled rate. Examples of classes of biologically active substances which may be incorporated in the sustained release compositions of the present invention include flavourings, pharmaceuticals, bacteriostats, viruscides, pesticides such as insecticides, nematicides, molluscicides and larvicides, herbicides, fungicides, algaecides, topical or dermatological agents, antifoulants for marine growth prevention, proteins, for example enzymes, peptides, microbiological and plant hydroculture salts and nutrients and preservations, veterinary trace metal formulations, and othe growth promoting factors used in animal husbandry: for example, anti-anaemia preparation and anabolic steroids. Of particular interest are compositions of the present invention comprising, as biologically active substance, at least one pharmaceutical.

The composition of this invention thus find wide application in medical and surgical, including veterinary, comtexts and in horticulture and agriculture as well as outside these areas.

There is no necessity for the active substance to be water soluble, although it will often possess some degree of water soluability what is required is that the active substance is soluble to an extent commensurate with its desired concentration (which, in the case of a biologically active substance, is related to this activity) in the controlled release composition of this invention in the water or organic solvent used to swell the hydrolysable hydrogel carrier on incorporation of the active substance therein.

Specific classes of medication system which may be used in a controlled release composition of the invention include abortificients such as prostaglandins, hypnotics, sedatives, tranquilisers, antipyretics, anti-inflammatory agents, antihistamines, anti-tussives, anticonvulsants, muscle relaxants, anti-tumor agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, preparations containing various substances for the treatment of infection by pathogens including anti-fungal agents, for example metronidazole, anti-parasitic agents and other anti-microbials, anti-malarials, cardiovascular agents, preparations containing hormones, for example androgenic, estrogenic and progestational hormones, notably steriods such as oestradiol, sympathomimetic agents, hypoglycaemic agents, contraceptives, nutritional agents, preparations containing enzymes of various types of activity, for example chymotrypsin, preparations containing analgesics, for example aspirin, and agents which many other types of action including nematocidesand other agents of veterinary application. Mixtures of active substances may be incorporated into the controlled relese composition.

The controlled release composition of this invention may be used as contraceptive composition suitably containing, as its active substance, at least one natural or synthetic steroid sex hormone for example an oestrogen or progestogen. Suitable progestogens include the natural progesterone and it synthetic analogues, including 11-dehydroprogesterone, delalutin, 21-fluoro-17-acetoxy-6-$\beta$-methylprogesterone, medroxyprogesterone acetate, megestrol acetate, chlormadinone acetate, ethisterone, dimethisterone, A-norprogesterone, 19-norprogesterone, 21-norprogesterone, normethandrone, norethynodrel, norethindrone and its acetate, DL- and D-norgestrel, norgestrienone, ethynodiol diacetate, lynstrenol, ethynylestradiol retroprogesterone, dydrogesterone, norvinodrel, quingestranol acetate, norethisterone and its acetate and oenanthate, anagesterone acetate, medrogestone, clomagestone, allyl estrenol and cingestol, preferably progesterone. Suitable oestrogens include the natural $\beta$-oestradiol and its synthetic analogues, principally ethinyloestradiol or mestranol, preferably $\beta$-oestradiol.

The controlled release compositions of this invention are also useful in the treatment of diabetes and pernicous anaemia where, for example, the controlled release of insulin and cobalamin, respectively, may be utilised.

Moreover, the controlled release compositions of this invention are particularly suited for the treatment, both prophylactic and therapeutic, of tropical diseases. Diseases which may be treated with the present compositions include malaria, leprosy, schistosomiasis and clonorchiasis. Examples of drugs which can be used as biologically active substances in sustained release compositions of this invention for the treatment of these and other tropical diseases include quinine, sulphonamides, rifamcin, clofazimine, thiambutosine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The controlled release compositions of this invention are also very well suited to veterinary applications. Examples include preparations of antibiotics for general antibacterial activity and also in the treatment of anaplasmosis in cattle. Also included are for provision of a wide spectrum of activity against both ectoparasites, for example termites and endoparasites including arthropods, arrested larvae stages of nematodes, lungworms and general strongyles: these may comprise avermectins. Another group encompassed are preparations for provision of activity against tremotode, cestode and roundworm infections: these may comprise amoscanate and praziquantel: preparations for provision of activity against theileria in cattle: these may comprise biologically active naphthoquinones such as menoctone. Also included are preparations for provision of activity against babesiosis in cattle, horses and dogs: these may comprise berenil, amidocarb and diampron. Another useful group is that of preparations for provision of activity against liver fluke in sheep and cattle and against Haemonchus species: these may comprise closantel.

The active substances may be incorporated into the carrier with this in dispersed form but is more preferably incorporated into the carrier after this has been formed into an appropriate physical format. Accordingly, the usual procedure for incorporation of the biologically active substance is for the carrier, in suitable physical form, to be swelled using a solution which may be aqueous. However, it is preferred, particularly with more readily hydrolysable carriers, that organic swelling agents are used. The use of organic swelling agents is also often required to solubilise the active substances; moreover, they can also have swelling characteristics enhanced over aqueous media. In some instances a completely non-aqueous organic solvent such as chloroform, ethanol/chloroform, tetrahydronaphthalene, nitrobenzene, methyl benzoate, butyrolactone or benzyl alcohol may be used. After swelling and absorption of the active substance, the controlled release composition may be dried to remove the solvent or alternatively may be used in the swollen form. It has been found that the swelling procedure, and in particular the proportion of swelling relative to the original volume which is allowed to take place, can have a quite significant effect upon the subsequent behaviour of the release composition in vivo, even though it may be dried before use. Preferably, therefore, the degree of swelling during incorporation of the biologically active substances lies between 150 parts per hundred and 700 parts per hundred of the original dry volume, particularly between 200 and 500 parts per hundred.

As indicated previously the carriers used in the present invention are hydrogels which may be used in an initially dry or initially swollen state and the mode of release differs in each case. The dry crystalline gels have the particular property not generally possessed by rubbery gels that on swelling, for example of a cylindrical pessary of the gel by body fluids, an outer shell of swollen or rubbery form is produced surrounding a core of crystalline material. This leads to certain particular advantages. Firstly, for an extended period a much mre uniform release of the substance is generally achieved in vivo as compared with the usual fairly rapid exponential or $t^{-\frac{1}{2}}$ fall off usually found with rubbery gels. Moreover, the pattern of release is very largely controlled by the nature of the carrier rather than the nature of the entire release composition, providing the active substance has a good water solubility and relatively low molecular weight, so that the formulation of such release compositions to give a particular release rate is considerably simplified. In the case of active substances of low water solubility and/or high molecular weight the release may be more dependent on the individual substance.

However, it is surprisingly found that fully swollen hydrogels of this invention can, after an initial surge of active substance, give uniform release. This profile is of great advantage in many medication systems, particularly with drugs of high therapeutic index.

The wet gels may function through the expulsion of the active substance from the release composition in a positive in vivo action consequent upon the occurrence of a rise in temperature from that at which the substance is stored and the consequent syneresis releasing solvent and the active substance from the carrier. It will be appreciated that this necessitates the incorporation of the active substance and storage of the controlled release composition at a temperature below that to which the carrier is subjected in use. Thus, for example, when the active substance is a pharmaceutical the carrier may conveniently be treated at 20° C. or less, for example at a temperature down to 0° C. or even as low as −19° C., with the solution of the pharmaceutical to effect the desired degree of swelling and uptake of the substance. Administration of the release composition so formed to a patient will then cause the temperature to rise to body temperature, which is about 37° C. in a human, and shrinkage of the polymer then occurs with expulsion of the solvent and active substance. In the event of any problems being encountered with respect to stability of the swollen gels, it is always possible to carry out the swelling shortly before use.

The present invention thus further comprises incorporating an active substance into a carrier as herein defined by swelling the carrier at one temperature with a liquid medium containing the substance, and thereafter utilising the swollen carrier in an environment at a second, higher, temperature thereby causing the expulsion of liquid medium and active substance from the swollen polymer. Moreover, the invention comprises administering to a human or non-human animal patient a composition comprising a biologically active substance and a carrier as herein defined, said composition being of a crystalline and/or swollen form.

The detailed nature of the procedure used for incorporating the biologically active substance into the carrier, including the physical format of the carrier is conveniently selected with a view to achieving the desired release characteristics. The carriers may be used as film or powder but are most often used in the form of a shaped body such as a hollow or blank cylinder, a sphere, a tablet or a slab and the nature of the shape and its dimensions may be selected appropriately. In this invention, primary target is to achieve a controlled release over an appropriate time period, conveniently of a major proportion, for example 80 or 90%, of the active substance. Release at a substantially constant rate, i.e. approximating to linear release, is an appropriate target in certain instances, this is provided to a considerable degree by the hydrogels of the present invention when in the form of a slab or flat sheet. Unusual release profiles may, however, be obtained by utilising carriers which comprise open cavities, for example hollow cylinders or slabs with one or more holes or hollows in them. It is found that the release profiles of such polymeric carriers can go through a maximum with time. Such geometric control of release profile provides very useful additional means of obtaining and controlling improved release profiles.

It has additionally been found that preferred carriers used in the present invention often exhibit a behaviour at their upper range of swelling which can be of assistance in maintaining a rate approximating to linear release for as long a period as possible. Thus it has surprisingly been found that the carrier, once swollen by a factor of about 10 times, will typically undergo spontaneous shrinkage back to a swelling level of only about 9 times. As the dry carrier swells in use, or as the wet carrier swells further, a boost to the rate of expulsion of the active substance is thereby given just at a time when this rate may be beginning to fall.

Moreover, the hydrolysis of the hydrogel will provide enhanced release of the active substance which will contribute either to the persistence of a linear release rate or, where the hydrolysis is rapid, to an initial maximum in the release rate.

Certain of the areas of pharmaceutical utility for compositions according to the present invention, are of special interest in such contexts. These include the administration of hormones, drugs for the treatment or prophylaxis of various conditions, e.g. substances having activity against pathogenic micro-organisms, are particularly suited to vaginal or rectal administration of the active substance and pessaries. The compositions may, however, be used for various localised applications in other parts of the body such as the treatment of maladies of the mouth or the eye, for example glaucoma. The compositions are also of interest for oral administration or in a topical patch to release a drug which can treat or be absorbed by the skin, and for use by implantation.

The mode of release from the wet polymer carriers may be employed in certain particular contexts. An example is in the treatment of maladies wherein a small dose of a drug requires to be released into the body each day. The temperature of the human body varies throughout the day, and generally follows a cycle. Since the degree of swelling of the polymer is dependent on the temperature, a swollen polymeric carrier having a solution of a suitable drug absorbed therein may be implanted into the body, and polymer will shrink and swell in response to the body temperature fluctuations. During periods of shrinkage, i.e. periods of rising temperature, increased portions of the absorbed drug will be ejected from the polymeric carrier into the bloodstream, thus providing a cyclical daily dosage of the drug.

The concentration of active substance incorporated into the controlled release composition of this invention can range from very high to very low. Thus, if a liquid biologically active material, such as m-cresol which swells the polymer to more than 1,000 pph, were used also to swell the polymer, then the active species could comprise more than 90% by weight of the release composition. A liquid which swelled to 1,000 pph and contained 25% of a drug could leave a loading of more than 70% of the drug in the dry polymer, and 30% to 70% loadings would be commonly attainable. Much lower loadings, e.g. 1.0% to 0.5% are also readily attainable.

The large degree of polymer swelling which is possible, and the small differences in temperature which occur in natural body temperature cycles, makes it possible for small doses of a drug to be positively ejected into the body daily over a long period of time. This feature is accordingly of interest in relation to the area, for example, of long-acting contraceptives of low water solubility.

Further specific applications of the wet polymers also exist outside the pharmaceutical field. One agricultural use is in the control of fermentation in silage. As this fermentation is accelerated by high temperature, an inhibitor which is activated by increased temperature is desirable. If swollen polyethylene oxide containing a fermentation inhibitor as the active substance is injected into the silage when the ambient temperature is low, an increase in the temperature will cause the polymer to shrink, releasing the inhibitor which then prevents or controls the fermentation of the silage.

The temperature dependence of the swelling of the polymer also makes it possible for trace elements or essential growth materials to be released into the soil on an annual and daily basis, as a summer temperature rise will cause swollen polyethylene oxide to release a solution of such an element or material absorbed therein. Treatment of soil with a composition of the present invention may therefore be effective over a number of years, depending on the degree of release occurring through a non-syneresis mechanism.

Other uses for the compositions of the present invention include the prevention of formation of slime such as algae in swimming pools by application of a slimicide (or algaecide) consequent upon the daytime temperature rise, and the inhibition of polymerisation through the release of a polymerisation inhibitor in response to a temperature rise in stored polymerisable monomers. In these cases, the active substance absorbed in the swollen polyethylene oxide is a slimicide (or algaecide) and a polymerisation inhibitor respectively. Controlled release compositions of this invention, in dry form, are also of interest in relation to their beneficial effect on the storage stability of potentially unstable compounds by incorporation into a crystalline matrix.

The general advantages of the polymeric carriers used in the present invention in the formulation of active substances, as compared with other polymers described in the art for this purpose, may be summarised as follows. The polymers are non-linear, cross-linked, high equivalent weight systems of an essentially insoluble nature as regards both water and a range of organic solvents which show a high degree of swelling with both aqueous and non-aqueous solvents and form tough materials in both the dry and wet forms (although naturally to a lesser extent in the latter case). The polymeric carriers also show a good profile of release which is controlled either by the crystallinity present in the dry gels or the syneresis effect obtainable with the wet polymers.

It will be appreciated that the present invention therefore further includes a controlled release composition which comprises an active substance and a polymeric carrier therefor, the carrier comprising polyethylene oxide and having the property of possessing crystallinity in the dry form and of exhibiting syneresis in the wet form. The term syneresis as used above means the property of undergoing a substantially greater level of swelling in an aqueous medium at 0° C. than at 100° C. Crystallinity is of assistance in accurate cutting of dry forms.

The ivention is illustrated by the following Examples.

EXAMPLES 1 to 37

2.443 g of hexane-1,2,6-triol (HT) (ex Aldrich Chem. Co.; dried in a vacuum oven for 24 hours at room temperature) were blended in a beaker with 0.5349 g of anhydrous ferric chloride (ex Aldrich Chem. Co.; further purified by sublimation in a cold finger condenser), as catalyst. The blend was then left to stand for 15 minutes at 90° C. 40 g of polyethylene oxide (PEO) (ex Hythe Chemicals Ltd.; dried for 4 to 5 hours in vacuo under a dry nitrogen purge) of number average molecular weight 3,100 were next mixed, with stirring, with the blend which was again left to stand for 15 minutes at 90° C. Distilled acrolein tetramer ($C_1$) (the gift of Canadian Industries Ltd.) was then added and stirred for 5 minutes. The acrolein tetramer was purified by triple distillation under reduced pressure and in a stream of dry nitrogen. In the last distillation, the initial fraction (10%) and the final fraction (20%) were discarded and the middle fraction, boiling between 78° and 80° C., was collected, under an inert atmosphere, into sealed glass ampules until use. The mixture was thereafter poured into preheated polypropylene moulds and cured by maintaining at 90° C. for 4.5 hours in a fume cupboard with an extractor fan.

The amount of ferric chloride catalyst comprised 0.1% of the total weight of reactants. The amount of hexanetriol comprised 1.394 mol. equivalent of the polyethylene oxide. The excess of acrolein tetramer used was 24%.

The mounds were removed from the oven and allowed to cool to room temperature. The hydrogel was taken out of the moulds; slices were cut therefrom; and their crystallinity and weight gain in water were determined. (The more rubbery hydrogels were cooled to −25° C. for about 2 hours before removal from their moulds).

Crystallinity was determined from an estimation of the heat of fusion (the heat of fusion of a polymer is proportional to the degree of crystallinity). The heat of fusion of the hydrogel was determined by measuring the heat required to melt the crystallites and the percentage crystallinity was calculated from the ratio of this value to that obtained from a completely crystalline sample. (As a completely crystalline sample was not available the heat of fusion of pure PEO was used. This has been determined as 220.12 $Jg^{-1}$. Braun et al. Kolloid Zeit. 215, 10, 1967.)

Fusion endograms of known weights (ca 10 to 40 mg) of the hydrogel samples were run in duplicate on a thermal analyser DuPont 910 and 119 model). The area under each fusion endogram was measured with a planimeter; and the heat of fusion calculated using the average measured area under the peak.

Weight gain in water was determined by immersing sample slices of known weight and thickness (ca. 1.35±0.2 mm) in distilled water and left at room temperature (ca. 20° C.) for about 24 hours. The slices were removed; blotted with a tissue and weighed.

The further Examples 2 to 37 were effected in essentially the same manner. Where tosylic (para-toluenesulphonic) acid (PTSA) (ex Fisons as monohydrate; water was removed by reflusing with 250 $cm^3$ toluene under a dry nitrogen bleed for 4 hours in a flask equipped with a Dean & Stark trap; concentrating; and freeze drying in vacuo.) was used as a catalyst, this comprised 0.35% of the total weight of reactants. Where PTSA was used, it was found necessary to elute the catalyst to prevent embrittlement of the hydrogel.

In Table 1 "BIF" means broken into fragments within 20 hours.

When hydrogels were prepared with PTSA they increased in crystallinity and became embrittled on standing for about 2 to 3 days (a somewhat longer period was observed when the hydrogel was frozen to about −25° C.). Embrittled samples did not readily hydrate but tended instead to disintegrate. This disadvantage could be completely overcome by immersing the freshly prepared polymer in water and drying (it is believed that this action leaches the catalyst). Hydrogels prepared with $FeCl_3$ did not exhibit this behaviour.

The crystallinity increased and water uptake decreased with increasing ratios both of HT and $C_1$. The use of excess $C_1$ was found to be a particularly useful technique enabling variation in crystallinity from ca. 56% to ca. 7% and water uptake from ca. 956% to ca. 103%. It seems clear from the results that $C_1$ is itself changing the polymer cross-linking density.

EXAMPLE 38

In this Example, two series each of seven hydrogels were prepared essentially as described in Example 1. Their compositions were as follows:

Series 1:
PEO ($\overline{M}_n$ = 3,100) + HT (1.394) + $C_1$   (1. stoichiometric)
(2. 9.789% excess)
(3. 17.27% excess)
(4. 24.03% excess)
(5. 57.8% excess)
(6. 12.5% excess)
(7. 200% excess)

Series 2:
PEO ($\overline{M}_n$ = 7,000) + HT (2) + $C_1$   (1. stoichiometric)
(2. 10% excess)
(3. 20% excess)
(4. 30% excess)
(5. 50% excess)
(6. 100% excess)
(7. 200% excess)

The swelling characteristics of the two series of hydrogels in distilled water at 21° C. were then studied by immersing small slabs of the hydrogels of known weight and dimensions (see Table 2) in distilled water at that temperature. The slabs were removed at set times of 1, 2, 3, 4, 8, 10, 20, 30, 60 minutes from initial immersion, blotted dry, weighed and reimmersed. This process was continued until equilibrium was attained.

The experiment was next repeated with selected hydrogels in distilled water at 37° C. as shown in Table 3.

The experiment was then repeated with selected hydrogels as shown in Table 4 using, as swelling agent, a 50:50 (w/w) mixture of ethanol and chloroform at 21° C.

EXAMPLE 39

In this Example, six 2.5 hydrogel slabs were prepared essentially as described in Example 1. 1.1 g of benzocaine (ethyl-4-aminobenzoate ex B.D.H. Chemicals Ltd.) was added to 500 ml of ethanol and chloroform (75:25 v/v) at room temperature (21° C.). The slabs were then swelled overnight (17 hours) in the drug solution at room temperature (see Table 5).

The swollen slabs were next removed, blotted dry and weighed. They were then dried in a vacuum oven for 3 days effectively leaving the drug loaded in an unswollen polymeric matrix. Three of the drug-loaded slabs (1, 2 and 3) were re-swelled in distilled water at 37° C. The slabs were removed at set times of 1, 2, 4, 8, 10, 20, 30, 60 minutes from initial immersion, blotted dry, weighed and reimmersed. This process was continued until equilibrium was attained.

The other three drug-loaded slabs (4, 5 and 6) were placed to a gauze container, immersed in 1,000 ml Sorensen's buffer solution at pH 7.5 at 37° C., and rotated at constant speed. As the drug diffused from the device it was rapidly dispersed into the bulk buffer solution by the rotation. Aliquots of the buffer solution were removed at set times of 3, 6, 10, 20, 30, 60 minutes from initial immersion and the UV absorbance at 285 nm was measured in a UV spectrophotometer (Perkin Elmer 551). Absorbance was calibrated by determining the absorbance of a range of buffer solutions containing known concentrations of benzocaine.

The experiment was next repeated with six 2.6 hydrogel slabs (see Table 6). After drying to leave benzocaine loaded in an unswollen hydrogel matrix the six slabs were then re-swelled overnight (16 hours) in the ethanol/chloroform benzocaine solution. Three fully swollen slabs (1, 2 and 3) were placed in the gauze container, immersed in the buffer solution and rotated as before. Aliquots were taken and the UV absorbance measured as before. The other three slabs (4, 5, and 6) were dried in a vacuum oven for 29 hours and then re-swelled in the gauze container, immersed in the buffer solution and rotated as before. Aliquots were taken and the UV absorbance measured as before.

The experiment was then repeated with six 2.7 hydrogel slabs (see Table 7) in essentially the same manner as the six 2.6 hydrogel slabs but with only one presentation to the benzocaine solution.

The results of Examples 38 and 39 are shown in the accompanying drawings in which.

TABLE 1

Figure 1:
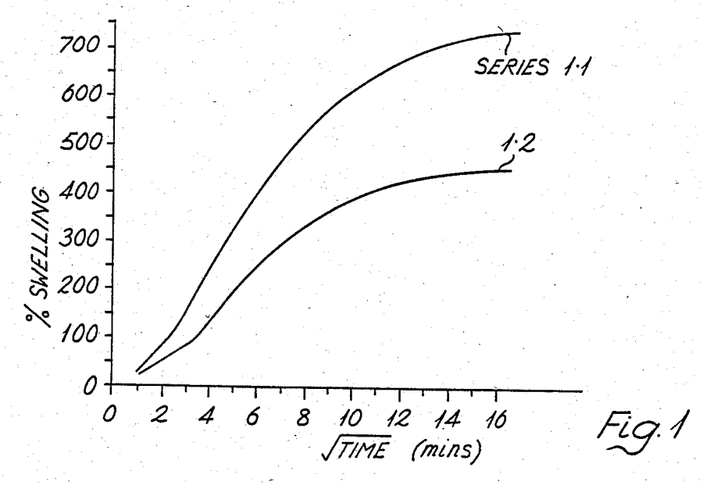
FIGS. 1 and 2 depict the percentage swelling of the polymer series 1 as a function of $(time)^{\frac{1}{2}}$.
Figure 2:
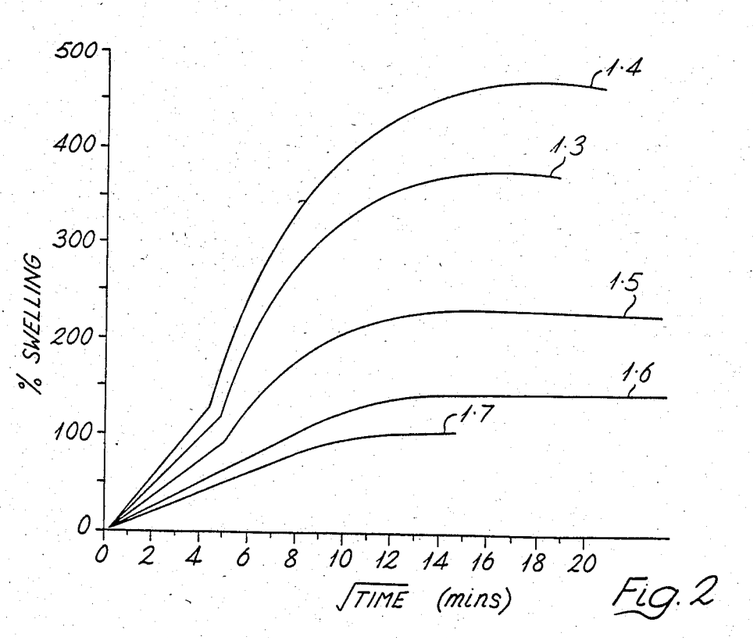
Figure 3:
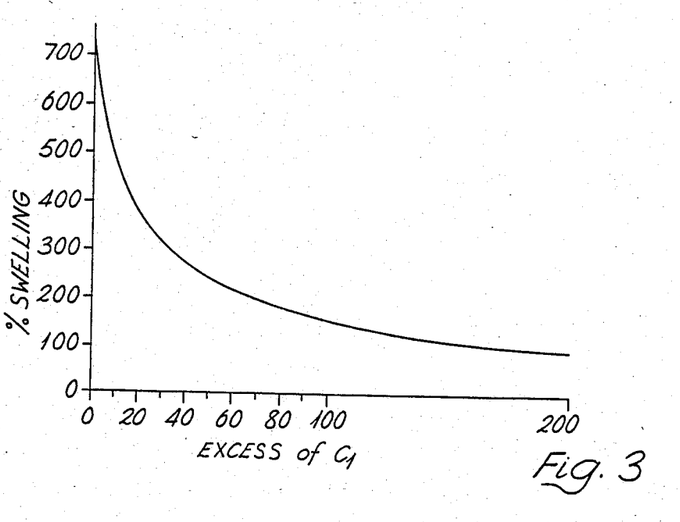
FIG. 3 depicts the percentage swelling of the polymer series 1 as a function of $C_1$ excess.
Figure 4:
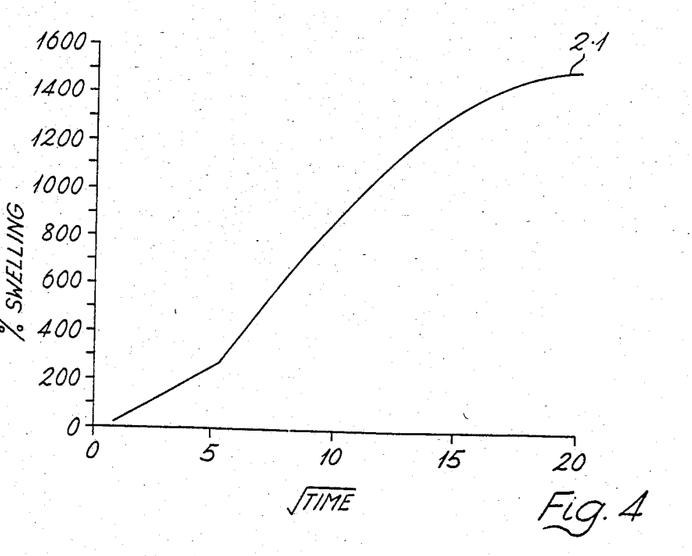
FIGS. 4 and 5 depict the percentage swelling of the polymer series 2 as a function of $(time)^{\frac{1}{2}}$.
Figure 5:
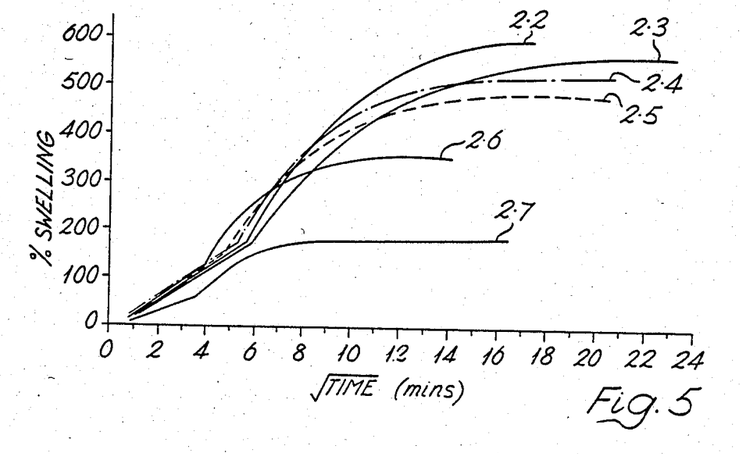
Figure 6:
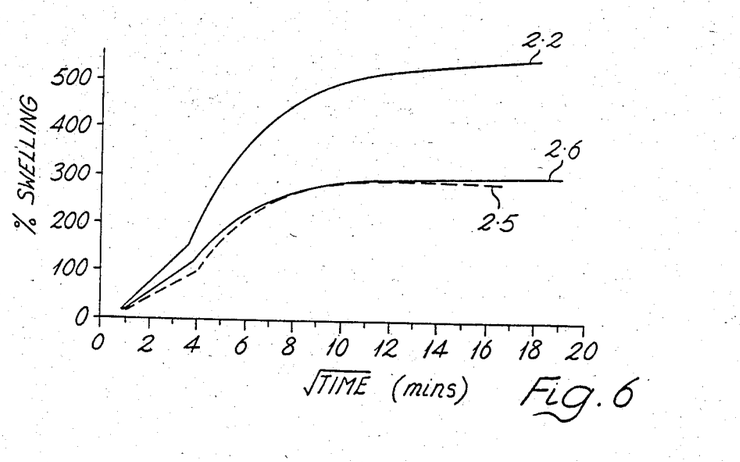
FIG. 6 depicts the percentage swelling of the polymer in Table 3 as a function of $(time)^{\frac{1}{2}}$.
Figure 7:
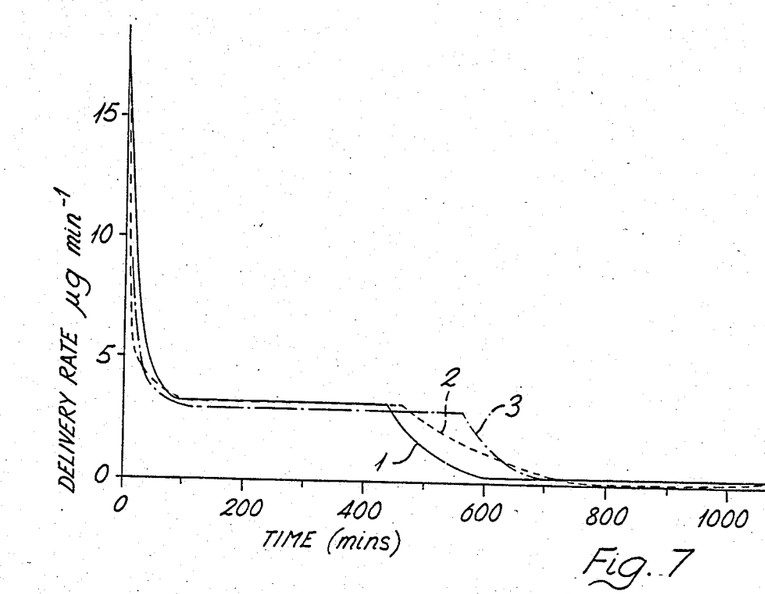
FIG. 7 depicts the in vitro delivery rate of benzocaine of the fully swollen polymer in Table 6 as a function of time.
Figure 8:
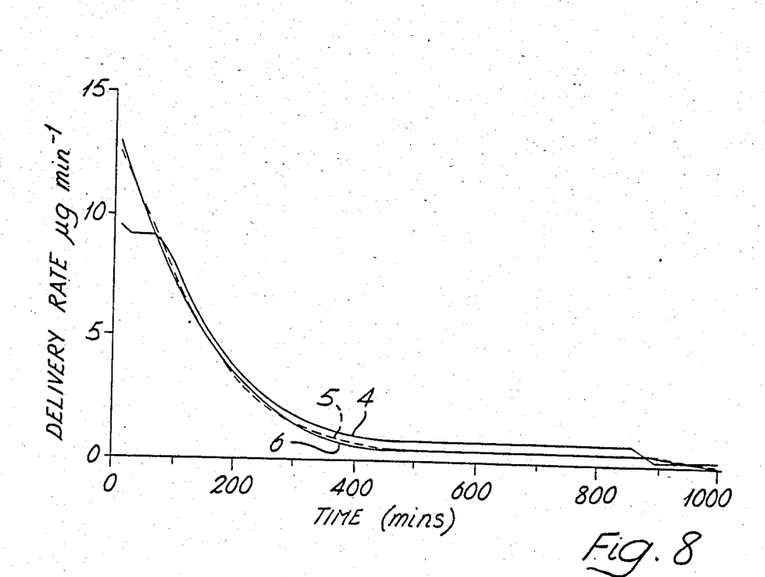
FIG. 8 depicts the in vitro delivery rate of benzocaine of the dried polymer of Table 6 as a function of time.
Figure 9:
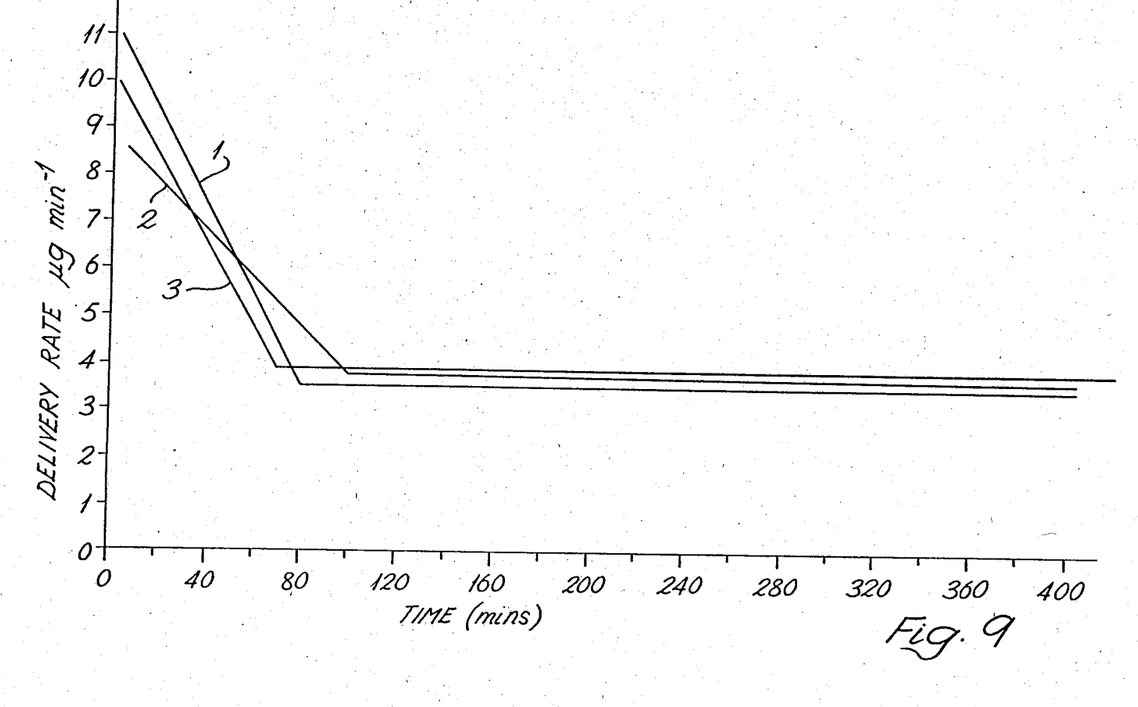
FIG. 9 depicts the in vitro delivery rate of benzocaine of the fully swollen polymer in Table 7 as a function of time.

| EXAMPLE NUMBER | PEO $\overline{M}n$ | PEO % by wt. | HT mole equiv. of PEO | EXCESS OF $C_1$ USED % | AVERAGE CRYSTAL- LINITY % | WEIGHT GAIN WHEN FULLY SWOLLEN IN WATER % | CATALYST USED |
|---|---|---|---|---|---|---|---|
| 2 | 8300 | 87.50 | 2.0 | ZERO | 71.45 | DISSOLVED | PTSA |
| 3 | 7000 | 93.47 | 0.5 | ZERO | 72.40 | DISSOLVED | PTSA |
| 4 | 7000 | 90.86 | 1.0 | ZERO | 61.70 | B.I.F. | PTSA |
| 5 | 7000 | 85.55 | 2.0 | ZERO | 56.50 | B.I.F. | PTSA |
| 6 | 7000 | 80.90 | 3.0 | ZERO | 74.03 | B.I.F. | PTSA |
| 7 | 7000 | 76.76 | 4.0 | ZERO | 80.89 | B.I.F. | PTSA |
| 8 | 7000 |  | 1.0 | 50.0 |  | B.I.F. | PTSA |
| 9 | 7000 | 79.02 | 2.0 | 100.0 |  | 369.4 | PTSA |
| 10 | 7000 | 73.43 | 2.0 | 200.0 |  | 373.5 | PTSA |
| 11 | 7000 | 82.26 | 2.0 | 50.0 | 49.36 | 444.6 | FeCl$_3$ |
| 12 | 7000 | 75.59 | 3.0 | 50.0 | 54.47 | 325.7 | FeCl$_3$ |
| 13 | 3100 | 79.12 | 1.394 | 2.187 | 90.68 72.16 | B.I.F. | PTSA |
| 14 | 3100 | 77.78 | 1.394 | ZERO | 63.79 | 329.3 | PTSA |
| 15 | 3100 | 77.78 | 1.394 | ZERO | 66.83 |  | PTSA |
| 16 | 3100 | 77.78 | 1.394 | ZERO | 57.41 | 392.7 | PTSA |
| 17 | 3100 | 77.78 | 1.394 | ZERO | 47.23 | 494.1 | PTSA |
| 18 | 3100 | 76.58 | 1.394 | 9.789 | 58.93 | B.I.F. | PTSA |
| 19 | 3100 | 75.42 | 1.394 | 17.27 | 59.67 | 155.1 | PTSA |
| 20 | 3100 | 73.13 | 1.394 | 24.03 | 70.61 | 136.4 | PTSA |
| 21 | 3100 | 73.13 | 1.394 | 24.03 | 56.14 | 315.6 | PTSA |
| 22 | 3100 | 73.13 | 1.394 | 24.03 | 48.22 |  | PTSA |
| 23 | 3100 | 68.09 | 1.394 | 57.86 | 38.85 |  | PTSA |
| 24 | 3100 | 68.09 | 1.394 | 57.86 | 51.22 | 210.2 | PTSA |
| 25 | 3100 | 68.09 | 1.394 | 57.86 | 72.17 | 115.6 | PTSA |
| 26 | 3100 | 63.77 | 1.394 | 125.51 | 48.67 | 226.5 | PTSA |
| 27 | 3100 | 63.77 | 1.394 | 125.51 | 43.90 | 223.7 | PTSA |
| 28 | 3100 | 63.77 | 1.394 | 125.51 | 64.59 | 121.7 | PTSA |
| 29 | 3100 | 79.16 | 1.394 | 2.187 | 56.77 | 956.0 | FeCl$_3$ |
| 30 | 3100 | 77.92 | 1.394 | Zero | 54.77 | 606.3 | FeCl$_3$ |
| 31 | 3100 | 76.51 | 1.394 | 9.789 | 49.59 | 388.5 | FeCl$_3$ |
| 32 | 3100 | 75.54 | 1.394 | 17.27 | 48.94 | 341.4 | FeCl$_3$ |
| 33 | 3100 | 70.69 | 1.394 | 57.86 | 32.47 | 218.3 | FeCl$_3$ |
| 34 | 3100 | 63.86 | 1.394 | 125.51 | 21.24 | 142.8 | FeCl$_3$ |
| 35 | 3100 | 57.72 | 1.394 | 200.0 | 7.34 | 103.2 | FeCl$_3$ |
| 36 | 3100 | 84.23 | 0.75 | ZERO | 55.10 |  | FeCl$_3$ |
| 37 |  | 83.15 | 0.75 | 10.0 | 52.99 |  | FeCl$_3$ |

The experiment was further repeated with six 2.6 hydrogel slabs (see Table 8) but with 23.64 g benzocaine being used. Three fully swollen slabs (2, 3 and 4) were placed in the gauze container, immersed in the buffer solution, and rotated as before. Aliquots were taken and the UV absorbance measured as before. The other three slabs (1, 5 and 6) were dried in a vacuum oven for 2 days and then re-swelled in the gauze container, immersed in the buffer solution and rotated as before. Aliquots were taken and the UV absorbance measured as before. After 1,000 minutes of release the Beer-Lambert law ceased to be obeyed and analysis was accordingly stopped.

TABLE 2

| Polymer | Weight (g) | Length (mm) | Width (mm) | Thickness (mm) |
|---|---|---|---|---|
| 1.2 | 0.3826 | 28 | 10 | 1.25 |
| 1.3 | 0.4020 | 29 | 10 | 1.36 |
| 1.4 | 0.3756 | 29 | 9 | 1.30 |
| 1.5 | 0.3653 | 27 | 10 | 1.36 |
| 1.6 | 0.4074 | 26 | 9.5 | 1.33 |
| 1.7 | 0.3398 | 25.5 | 9.5 | 1.27 |
| 2.1 | 0.3449 | 23 | 10 | 1.39 |
| 2.2 | 0.3829 | 25 | 9 | 1.40 |
| 2.3 | 0.4305 | 26 | 9.5 | 1.38 |
| 2.4 | 0.3827 | 25 | 10 | 1.37 |

TABLE 2-continued

| Polymer | Weight (g) | Length (mm) | Width (mm) | Thickness (mm) |
|---|---|---|---|---|
| 2.5 | 0.3612 | 25.5 | 9 | 1.30 |
| 2.6 | 0.2778 | 27 | 9 | 1.01 |
| 2.7 | 0.2999 | 26 | 10 | 1.02 |

TABLE 3

| Polymer | Weight (g) | Length (mm) | Width (mm) | Thickness (mm) |
|---|---|---|---|---|
| 2.2 | 0.3863 | 28 | 9.5 | 1.36 |
| 2.2 | 0.3850 | 28 | 10 | 1.36 |
| 2.2 | 0.3853 | 28 | 9.5 | 1.36 |
| 2.5 | 0.3841 | 29 | 10 | 1.34 |
| 2.5 | 0.3820 | 28 | 10 | 1.34 |
| 2.5 | 0.3851 | 28 | 9.5 | 1.34 |
| 2.6 | 0.3793 | 28 | 10 | 1.30 |
| 2.6 | 0.3777 | 28 | 10 | 1.30 |
| 2.6 | 0.3791 | 28 | 10 | 1.31 |

TABLE 4

| Polymer | Weight (g) | Length (mm) | Width (mm) | Thickness (mm) |
|---|---|---|---|---|
| 1.1 |  | 28 | 10 | 1.33 |
| 1.2 | 0.3584 | 27 | 9 | 1.20 |
| 1.3 | 0.3721 | 29 | 10 | 1.27 |

TABLE 5

| | Weight (g) | Length (mm) | Width (mm) | Thickness (mm) | Dry weight (g) | Wet weight (g) |
|---|---|---|---|---|---|---|
| 1 | 0.3744 | 29 | 9 | 1.345 | 0.3486 | 1.2645 |
| 2 | 0.3796 | 28.5 | 9 | 1.345 | 0.3567 | 1.2751 |
| 3 | 0.3741 | 29 | 9 | 1.345 | 0.3525 | 1.2570 |
| 4 | 0.3745 | 29 | 10 | 1.335 | 0.3515 | 1.3240 |
| 5 | 0.3783 | 27.5 | 10 | 1.34 | 0.3548 | 1.2625 |
| 6 | 0.3745 | 29 | 10 | 1.335 | 0.3508 | 1.3027 |

TABLE 6

| | Weight (g) | Length (mm) | Width (mm) | Thickness (mm) | Dry weight after 29 hrs (g) | Wet weight in $CHCl_3$/$C_2H_5OH$ + drug (g) |
|---|---|---|---|---|---|---|
| 1 | 0.3800 | 28.5 | 9.5 | 1.34 | 0.3466 | 1.4035 |
| 2 | 0.3832 | 29 | 9 | 1.34 | 0.3543 | 1.4825 |
| 3 | 0.3857 | 28.5 | 9 | 1.34 | 0.3655 | 1.3916 |
| 4 | 0.3859 | 28.5 | 9.5 | 1.345 | 0.3630 | 1.3900 |
| 5 | 0.3818 | 29 | 9.5 | 1.345 | 0.3622 | 1.3800 |
| 6 | 0.3858 | 28.5 | 9.5 | 1.34 | 0.3661 | 1.3800 |

TABLE 7

| | Initial weight (g) | Length (mm) | Width (mm) | Thickness (mm) | Wet weight (g) | Dry weight (g) |
|---|---|---|---|---|---|---|
| 1 | 0.4295 | 28 | 10 | 1.355 | 1.1242 | |
| 2 | 0.4248 | 29 | 10.5 | 1.35 | 1.1045 | |
| 3 | 0.4254 | 28.5 | 10.1 | 1.355 | 1.1123 | |
| 4 | 0.4218 | 29 | 10 | 1.35 | 1.0857 | 0.4225 |
| 5 | 0.4236 | 28.5 | 10.5 | 1.35 | 1.0838 | 0.4243 |
| 6 | 0.4292 | 28 | 10 | 1.355 | 1.0992 | 0.4287 |

TABLE 8

| | Weight (g) | Length (mm) | Width (mm) | Thickness (mm) | Wet weight (g) | Dry weight (g) |
|---|---|---|---|---|---|---|
| 1 | 0.4094 | 27 | 10 | 1.43 | 2.5744 | 0.4693 |
| 2 | 0.4058 | 28.5 | 9.5 | 1.425 | 1.5625 | |
| 3 | 0.4081 | 28.5 | 9.5 | 1.42 | 1.7255 | |
| 4 | 0.4058 | 28.5 | 9.5 | 1.425 | 1.5760 | |
| 5 | 0.4005 | 28.5 | 9 | 1.42 | | 0.4692 |
| 6 | 0.4058 | 29 | 9.5 | 1.42 | | 0.4749 |

I claim:

1. A controlled release composition which comprises:
   (a) an active substance, and
   (b) a carrier therefor comprising a hydrogel comprising polymerised moieties derivable from (i) at least one polymerisable cyclic (thio)ether and (ii) at least one hydrophilic homo- or copolymer.

2. A controlled release composition according to claim 1 wherein the active substance comprises a medication system.

3. The controlled release composition according to claim 1 wherein the medication system comprises a compound selected from the group consisting of
   a hypnotic,
   a sedative
   a tranquilizer,
   an anti-pyretic,
   an anti-inflammatory agent
   an anti-histamine,
   an anti-tussive,
   an agent for the treatment of malignant neoplastia,
   a topical or dermatological agent,
   a diuretic agent,
   an anti-depressant,
   an anti-fungal agent,
   a steroid and
   an analgesic.

4. The controlled release composition according to claim 1 in the shape of a cylinder, film or slab.

5. The controlled release composition according to claim 1 wherein the cylinder is hollow or the film or slab has one or more holes or hollows therein to modify the release properties.

6. A controlled release composition according to claim 1 wherein the active substance comprises a compound selected from the group consisting of
   a fungicide,
   an algaecide,
   a herbicide,
   a nematocide, and
   an insecticide.

7. A controlled release composition according to claim 1 wherein the active substance comprises a polymerisation inhibitor.

8. A process for the preparation of a controlled release composition according to claim 1 which comprises
   (a) fabricating a hydrogel as defined in claim 1 in any desired form;
   (b) contacting the hydrogel with a solution of an active substance and permitting it to swell therein; and
   (c) removing the swollen hydrogel from the solution.

9. The process according to claim 8 wherein the permitted swelling of the hydrogel is from 200 to 700 parts by volume per hundred of the initial dry volume.

10. The process according to claim 8 wherein the swelling is effected at a temperature from $-20°$ C. to $+20°$ C.

11. A method of controlled administration to a human or non-human animal patient of a biologically active substance other than a prostagland in which comprises
(a) incorporating the active substance into a controlled release composition according to claim 1; and (b) applying the composition to the part of the patient to be treated.

12. The process of claim 8 further comprising:
(d) drying the swollen hydrogen, thereby providing a controlled release composition comprising the active substance.

* * * * *